(12) United States Patent
Nowak

(10) Patent No.: US 6,941,797 B2
(45) Date of Patent: Sep. 13, 2005

(54) DEVICE AND METHOD FOR DETERMINING THE VISCOSITIES OF LIQUIDS BY MEANS OF THE CAPILLARY FORCE

(75) Inventor: Stephan Nowak, Köln (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/632,753

(22) Filed: Aug. 1, 2003

(65) Prior Publication Data

US 2004/0025572 A1 Feb. 12, 2004

(30) Foreign Application Priority Data

Aug. 7, 2002 (DE) .......................... 102 36 122

(51) Int. Cl.⁷ .............................. G01N 11/06
(52) U.S. Cl. .................. 73/54.07; 73/54.04; 73/54.08; 73/54.01
(58) Field of Search .............. 73/54.07, 54.05, 73/54.08, 54.04, 53.01, 54.01

(56) References Cited

U.S. PATENT DOCUMENTS

| | | | | |
|---|---|---|---|---|
| 1,637,386 A | * | 8/1927 | Russell | 73/54.01 |
| 4,554,821 A | * | 11/1985 | Kiesewetter et al. | 73/54.07 |
| 5,447,440 A | * | 9/1995 | Davis et al. | 435/6 |
| 5,792,941 A | * | 8/1998 | Rye et al. | 73/53.01 |
| 6,488,896 B2 | * | 12/2002 | Weigl et al. | 422/101 |
| 6,523,396 B2 | * | 2/2003 | Shin et al. | 73/54.04 |
| 6,581,438 B1 | * | 6/2003 | Hall et al. | 73/53.01 |
| 6,598,465 B2 | * | 7/2003 | Shin et al. | 73/54.07 |
| 6,681,616 B2 | * | 1/2004 | Spaid et al. | 73/54.07 |
| 6,732,574 B2 | * | 5/2004 | Hajduk et al. | 73/54.05 |
| 2002/0184941 A1 | * | 12/2002 | Shin et al. | 73/54.01 |

OTHER PUBLICATIONS

Din En Iso 9514, Aug. 1994, "Bestimmung der Tropfzeit von flüssigen Systemen".

Ultrasonics 36, (month unavailable) 1998, pp. 483–490, E. v. d. Burg, Z. Kojro, W. Grill, Synchronous determination of the rheological and acoustic properties of fluids using an oscillating fiber sensor and an ultrasonic microscope with phase contrast.

* cited by examiner

Primary Examiner—Michael Cygan
(74) Attorney, Agent, or Firm—Joseph C. Gil

(57) ABSTRACT

The invention relates to a device and a method for automated and simultaneous determination of the viscosity of a plurality of liquids.

15 Claims, 2 Drawing Sheets

Fig. 1(b)
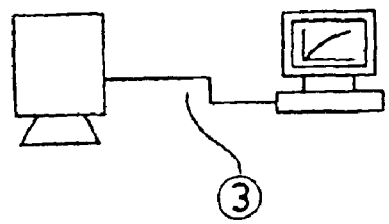
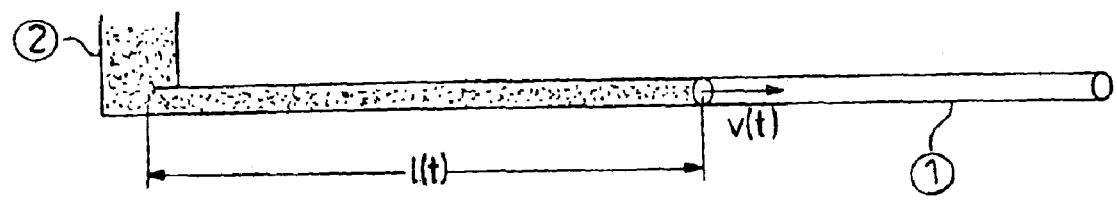
Fig. 1(a)
Fig. 2
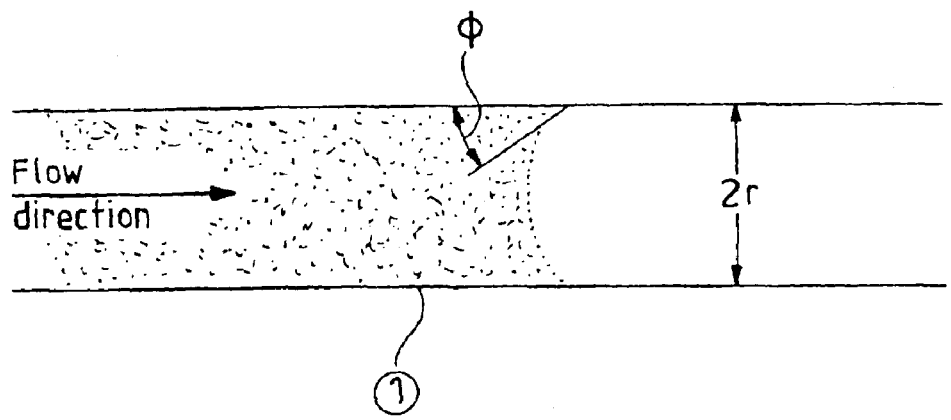

DEVICE AND METHOD FOR DETERMINING THE VISCOSITIES OF LIQUIDS BY MEANS OF THE CAPILLARY FORCE

CROSS REFERENCE TO RELATED PATENT APPLICATION

The present patent application claims the right of priority under 35 U.S.C. §119 (a)–(d) of German Patent Application No. 102 36 122.3, filed Aug. 7, 2002.

FIELD OF THE INVENTION

The invention relates to a device and a method for automated and simultaneous determination of the viscosity of a plurality of liquids.

BACKGROUND OF THE INVENTION

In the development of coatings, the viscosity of the initial formulation as well as the curing behaviour of the batch is affected by, for example, variation of catalysts, binders, curers or solvents. For processing, however, for example in a spray gun, it is necessary for the viscosity to vary in a particular range.

For the processing of systems which cure, for example in the field of two-component (2C) coatings, this gives rise to a time limitation, the so-called "pot life", after the expiration of which the coating is no longer processable since its viscosity has increased too much. The pot life in this case reflects the period of time between mixing of the binder and curer and the time when the material is no longer processable. In the development of new coating systems, it is therefore necessary for them to have a controlled pot life.

For the development of coatings using methods from combinatorial chemistry, large quantities of different substances to be tested are encountered within a short time, the available quantity of substance generally being limited to a few grams. In technical coating development, the method according to DIN EN ISO 9514 is customarily used for determining the pot life. A special vessel with a fixed volume (standard flow beaker) is filled with a substance, which then flows out through a hole in the bottom of the vessel. The flow time is measured. The pot life is determined by the increase in the flow time by a particular factor, generally twice the initial value. Flow beakers are calibrated using newtonian liquids of known viscosity.

Commercially available viscosimeters operate according to various functional principles, as described for example in Brock/Groteklaes/Mischke, Lehrbuch der Lacktechnologie, Vincentz Verlag Hanover 1998.

Capillary viscosimeters, for example Ubbelohde viscosimeters, are instruments for determining the kinematic viscosity of liquids.

The liquid is forced at a defined pressure through a capillary of particular length and particular radius. Either the time taken for a particular volume to flow through is measured or, conversely, the volume which flows through during a particular time is measured. The liquid may in this case be forced or sucked through the capillary. For low-viscosity liquids, the operating pressure can be generated simply by gravity with a storage vessel being placed at a raised height. The evaluation is carried out according to the Hagen-Poisseuille law:

$$\frac{dV}{db} = \frac{\pi \cdot r^4}{8\eta l}\Delta p. \tag{1}$$

The falling ball viscosimeter (Höppler viscosimeter) consists of a glass measuring tube, which holds the liquid to be tested and 6 balls. The fall time of the balls between two measuring markers is determined, and the dynamic viscosity of the liquid can be calculated from this via the density difference between the balls and the liquid and an equipment constant.

Another way of determining the rheology of substances is provided by the rheometer. In this case, a layer of the liquid is placed, and sheared, between two bodies of defined geometry. Inter alia, the viscosity can be determined from the response of the liquid to shearing. Examples of conventional geometries are plate/plate, plate/tip, plate/spherical shell or concentric cylinders. An advanced method for determining rheological parameters is described, for example, in Ultrasonics 36 (1998), pages 483–490.

Disadvantages with all the described methods are that the instruments only operate serially, the measurements sometimes last a very long time, for example rheometers, and the measuring instruments need to be cleaned after each measurement.

It was an object of the present invention to provide a purely qualitatively operating method for determining viscosities, with which a large number of samples can be evaluated within a short time. The equipment developed for carrying out this method should in this case make it possible to evaluate a fairly large number of samples in parallel and avoid onerous cleaning of the equipment components, in particular the measuring capillaries. The data acquisition should in this case be carried out as automatically as possible.

SUMMARY OF THE INVENTION

This object is achieved through the use of capillary action, by bringing a horizontally arranged capillary into contact with a liquid reservoir and subsequently determining the distance and velocity of the liquid column, which advances owing to the capillary action in the horizontal capillary.

The present invention therefore relates to a method for determining the viscosities of liquids by means of a capillary, characterised in that a horizontally arranged transparent capillary, which is open on both sides, is connected at one end of the capillary to a reservoir containing the liquid to be measured, and the velocity and the distance of the liquid column in the capillary are subsequently registered. The method according to the invention is used for simultaneous comparative determination of the viscosities of a plurality of liquids in the scope of screening.

BRIEF DESCRIPTION OF THE DRAWINGS

The invention is further described by the following non-limiting drawings in which:

FIGS. 1(a) and 1(b) are schematic diagrams which depict an overview of the system of the present invention including the capillary and reservoir (FIG. 1(a) and the electronic evaluation unit (FIG. 1(b)).

FIG. 2 is enlargement of the capillary shown in FIG. 1(a).

DETAILED DESCRIPTION OF THE INVENTION

Figure 3:
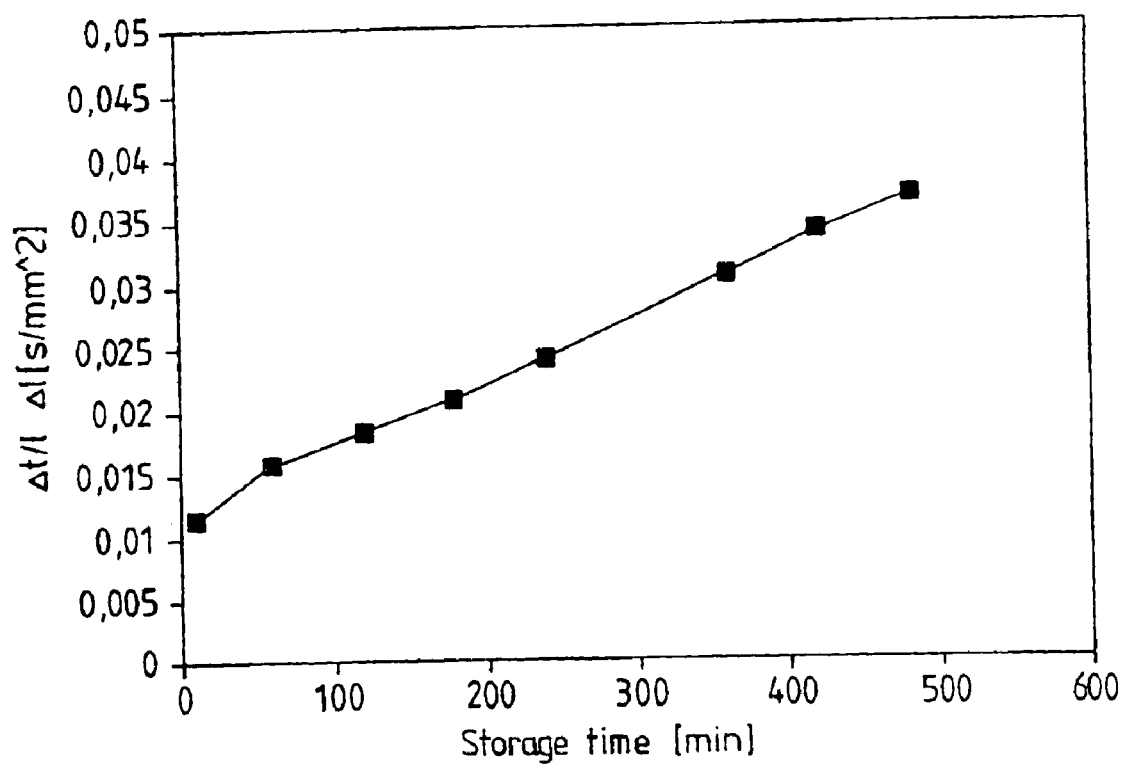
FIG. 3 is a graph of the relationship of viscosity and time after coating (storage time).

The method according to the invention makes use of capillary action. A transparent capillary which is open on both sides is arranged horizontally, and is brought into communication at one end with a small reservoir of the liquid to be determined. The liquid is drawn into the capillary by capillary action; this takes place commensurately faster when the viscosity of the liquid in question is lower. The position of the liquid column and the distance travelled in the capillary are registered electronically. The liquids suitable for the method according to the invention are liquids with wetting properties.

The function of the described arrangement can be explained with the aid of the forces engaged on the liquid column. FIGS. 1(a) and 1(b) depicts an overview of the arrangement, in which the capillary (1), the reservoir (2) (FIG. 1(a)) and an electronic evaluation unit (3) (FIG. 1(b)) are represented. The region of the liquid surface is represented on an enlarged scale in FIG. 2. The meniscus is characterised by the edge angle φ, and the capillary itself has a radius r. The edge angle φ is characteristic of the material pair comprising liquid/capillary material. The surface of the liquid column advances with a velocity v and has a length I. These two quantities are time-dependent and will be denoted below by v(t) and I(t).

Various forces act on the liquid column, on the one hand the capillary force ($F_K$) defined by Equation (2):

$$F_K = 2\sigma r \pi^* \cos \phi = C^* r \quad (2)$$

Here, r is the radius of the capillary, π is the number pi, σ is the so-called specific surface energy and φ is the edge angle introduced in FIG. 2. Since φ and σ are constant for the material pair comprising capillary material/liquid, they can be combined together with the other constants in the equipment constant C.

The capillary force is opposed by the frictional force of the liquid column on the glass capillary. This is defined by Equation (3) in the case of laminar flow:

$$F_R(t) = 8\pi \eta l(t) v(t) \quad (3).$$

Here, 1 is the instantaneous length of the liquid column, v is its velocity, and η is the viscosity of the liquid. According to the "action =reaction" law, the two forces can be set equal and solved for η. This gives Equation (4):

$$\eta = \frac{Cr}{8\pi l(t) v(t)}. \quad (4)$$

This equation contains only constants—apart from the quantities l(t) and v(t), so that the product l(t)v(t) must also be constant as a function of time as soon as laminar flow has been established in the capillary. This is the case after a few seconds in a real measurement, and it is immediately recognisable since the product l(t)v(t) no longer changes while the liquid continues to flow in the capillary. This can be used during the viscosity measurement in order to achieve greater statistical reliability by multiple determination of the characteristic value. The different measurement values obtained in the initial phase of the measurement can also be identified easily in an automated fashion and eliminated in an automated fashion.

In practice, the viscosity determination according to the above formula is accomplished as follows: The instantaneous velocity v(t) is approximated by the average velocity Δl/Δt in a time interval Δt. In a measurement, either the length of the liquid column l(t) is measured at the spacing of small time intervals (small compared with the total time which the liquid requires to migrate through the capillary), or the time intervals which the liquid column respectively takes to advance by a fixed length section are determined. This gives l(t) and the approximated quantity v(t). The following equation is then obtained with Formula (4):

$$\eta = \frac{Cr\Delta t}{8\pi l(t) \Delta l(t)} = \frac{Cr}{8\pi} \cdot \frac{\Delta t}{l(t) \Delta l(t)}, \quad (5)$$

where, in the right-hand part of the right-hand side of Eq. (5), all the constants are combined in the first term and all the time-variable quantities, that is to say those which are being measured, are combined in the second term. The first term is therefore merely a constant proportionality factor.

A relationship with viscosities which have been obtained by means of the flow beaker method can be established using a calibration curve which only needs to be determined once.

The present invention also relates to a device for carrying out the method according to the invention, characterised by at least one horizontally arranged transparent capillary, which is open at both ends and is connected, at one end, to a reservoir containing the liquid to be measured, the capillary and the reservoir forming a capillary-reservoir unit, and an electronic evaluation unit for determining the velocity and the distance of the liquid column in the capillary. A preferred device contains from 2 to 10, preferably from 2 to 5 capillary-reservoir units.

The capillaries to be used according to the invention are made of a transparent material, for example glass or plastic; it is preferable to use glass capillaries. The shape of the capillaries is generally rectilinear, and the respective internal diameter constant over the relevant length. The diameter is from 0.1 to 1 mm, preferably from 0.3 to 0.5 mm. It is preferable to use so-called single-use capillaries for the method according to the invention.

The device according to the invention is preferably arranged on a support. The support itself may be made of various materials, for example plastic, glass, wood or metal, preferably of plastic. The support is particularly preferably made of a solvent-resistant plastic material, for example Teflon; black eloxed aluminium is likewise preferred. For better positioning of the capillaries, the support may optionally be provided with grooves or slots, or optionally with an indentation for positioning of the reservoir.

According to the invention, either the reservoir is a drop of the liquid to be determined, which is placed in an indentation on the support, or the reservoir is a container which contains the liquid to be determined. These containers may, for example, be small pots or bowls. The reservoir has a volume of from 0.1 to 1 ml, preferably from 100 to 300 μl. It is preferable to use a container. Overall, the liquid level in the reservoir must be low enough so that no hydrostatic pressure can build up at the lower end of the reservoir.

If a container is being used as the reservoir in the device according to the invention, it may be incorporated in the support or put on the support or form one piece with the support. The capillary can be connected to the support in a variety of ways, for example by adhesive bonding or mounting; the capillary is preferably placed in grooves of the support.

The liquid to be determined may, for example, be delivered to the device according to the invention by a manually operated pipette or by a pipetting machine. Other delivery devices may also be used, the liquid reaching the reservoir as a result of flow or shaking. Delivery by means of a pipetting machine is preferred.

The velocity and the distance are registered according to the invention by means of an electronic evaluation unit. In this case, measurements are taken at least at two different positions of the capillary.

One way of registering involves observing the capillary with a camera and evaluating the camera image by using image evaluation methods in real time or, after having carried out the experiment, with temporary storage of the raw data.

Another way of registering involves shining light through the capillary and registering the shadow of the liquid column by means of a linear photodetector arrangement fitted behind the capillary. It is likewise possible to dope the liquids by means of a fluorescent dye and read the position of the liquid column using a fluorescence detection method. Cameras are again in principle suitable for this, as are, for example, fluorescence detectors for detecting fluorescence in microtitre plates (MTPs), so long as the fluorescence detectors are freely configurable in terms of geometry. The device may be illuminated from the side, from above or from below, optionally through a slot.

The preferred registration is carried by using a camera with a computer-controlled image evaluation unit.

The method according to the invention makes it possible to comparatively determine the viscosities of a plurality of substances simultaneously, so that a direct comparison of the development of the viscosity during curing of the coatings is possible.

A particular advantage of the invention is that it is not necessary to clean any sensitive parts of the equipment. It is therefore also possible to work with substances which cure very quickly and which set in the capillary during the measurement.

By using so-called "disposable" elements, the risk of cross-contamination between substances is furthermore reduced or fully eliminated.

The method according to the invention can be used wherever comparative viscosity measurements need to be carried out on different substances. These may be both viscosity comparisons of different substances at the same time, as well as recordings of the viscosity development of the same substance at different times.

The method according to the invention, or the device, can be used and applied for materials research, for example for coatings, ingredients for coatings or other liquid formulations, in pharmaceutical research, for the production of liquid products, for example on-line analysis or monitoring of liquid ingredients for production.

EXAMPLES

The measurement was carried out on a conventional 2C coating, specifically 4 h after formulation. An average of (0.024+/−0.003) s/mm02 is obtained for the quantity $\Delta t/(l(t) \Delta l(t))$. This quantity is—apart from the constant factor—exactly proportional to the actual viscosity of the substance.

TABLE 1

Value table of an exemplary embodiment of the viscosity determination according to the invention

| l | lΔ | t | Δt | Δt/(l(t) Δl(t)) |
|---|----|---|----|-----------------|
| 15 | — | 3 | — | — |
| 20 | 5 | 5 | 2 | 0.02 |
| 25 | 5 | 8 | 3 | 0.024 |
| 30 | 5 | 12 | 4 | 0.026666667 |
| 35 | 5 | 16 | 4 | 0.022857143 |
| 40 | 5 | 21 | 5 | 0.025 |
| 45 | 5 | 26 | 5 | 0.022222222 |

TABLE 1-continued

Value table of an exemplary embodiment of the viscosity determination according to the invention

| l | lΔ | t | Δt | Δt/(l(t) Δl(t)) |
|---|----|---|----|-----------------|
| 50 | 5 | 33 | 7 | 0.028 |
| 55 | 5 | 38 | 5 | 0.018181818 |
| 60 | 5 | 45 | 7 | 0.023333333 |
| 65 | 5 | 53 | 8 | 0.024615385 |
| 70 | 5 | 62 | 9 | 0.025714286 |
| 75 | 5 | 70 | 8 | 0.021333333 |
| 80 | 5 | 81 | 11 | 0.0275 |

If a plurality of these measurements are carried out at different times (storage time) after formulation, a curve of the viscosity increase of the coating after formulation can be plotted (FIG. 3).

In order to achieve "calibration" of the viscosity values obtained in this way, for example with respect to values obtained by the flow beaker method, it is sufficient to collate the relevant values next to one another in a table, or to plot a calibration curve from such value pairs.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for determining the viscosities of liquids using a capillary comprising:
   providing a horizontally arranged transparent rectilinear capillary tube, which is open on both sides, and connected at one end of the capillary to a reservoir containing the liquid to be measured,
   allowing the liquid to move along the capillary under capillary action only, and
   measuring the velocity and the distance of the liquid column in the capillary at time intervals.

2. The method according to claim 1, wherein the viscosities of a plurality of liquids are determined in parallel.

3. A device for determining the viscosities of liquids utilizing the method according to claim 1 comprising at least one horizontally arranged transparent rectilinear capillary tube which is open at both ends and is connected, at one end, to a reservoir containing the liquid to be measured, the capillary and the reservoir forming a capillary-reservoir unit, and a camera with a computer-controlled image evaluation unit for measuring the velocity and the distance of the liquid column in the capillary, which moves along the capillary under capillary action only.

4. The device according to claim 3, characterised in that it contains from 2 to 10 capillary-reservoir units.

5. The device according to claim 3 characterised in that the diameter of the capillaries is from 0.1 to 1 mm.

6. The device according to claim 3, characterised in that the capillary is a single-use capillary.

7. The device according to claim 3, characterised in that the device is arranged on a support.

8. The device according to claim 3, characterised in that the reservoir is a container and has a volume of from 0.1 to 1 ml.

9. The device according to claim 3, characterised in that the camera with a computer-controlled image evaluation unit includes a fluorescence detection method.

10. The device according to claim 4 characterised in that the diameter of the capillaries is from 0.1 to 1 mm.

11. The device according to claim 4, characterised in that the capillary is a single-use capillary.

12. The device according to claim 5, characterised in that the capillary is a single-use capillary.

13. The device according to claim 3, characterised in that the camera with a computer-controlled image evaluation unit includes a fluorescence detection method.

14. The device according to claim 4, characterised in that the camera with a computer-controlled image evaluation unit includes a fluorescence detection method.

15. The device according to claim 5, characterised in that the camera with a computer-controlled image evaluation unit includes a fluorescence detection method.

* * * * *